(12) United States Patent
Chan et al.

(10) Patent No.: US 6,358,262 B1
(45) Date of Patent: Mar. 19, 2002

(54) LAMELLAR DISSECTING INSTRUMENT

(75) Inventors: Kwan Y. Chan, Fort Worth; Gregory S. Milios, Arlington, both of TX (US); David E. Booth, Wyomissing Hills; Dyson W. Hickingbotham, Stouchsburg, both of PA (US)

(73) Assignee: Alcon Universal Ltd., Hunenberg (CH)

( * ) Notice: Subject to any disclaimer, the term of this patent is extended or adjusted under 35 U.S.C. 154(b) by 0 days.

(21) Appl. No.: 09/467,462

(22) Filed: Dec. 20, 1999

Related U.S. Application Data

(63) Continuation-in-part of application No. 09/434,912, filed on Nov. 5, 1999.

(51) Int. Cl.⁷ .................................................. A61F 9/00
(52) U.S. Cl. ....................................................... 606/166
(58) Field of Search .............................. 606/166–167, 606/107, 161, 162; 216/24

(56) References Cited

U.S. PATENT DOCUMENTS

| | | | |
|---|---|---|---|
| 3,980,086 A | 9/1976 | Kletschka et al. | 128/318 |
| 4,586,491 A | 5/1986 | Carpenter | 128/6 |
| 4,642,090 A | 2/1987 | Utrata | 604/22 |
| 4,858,324 A | 8/1989 | Wiech, Jr. | 30/357 |
| 4,887,598 A | 12/1989 | Berle | 606/180 |
| 4,985,030 A | 1/1991 | Melzer et al. | 606/51 |
| 5,195,541 A | 3/1993 | Obenchain | 128/898 |
| 5,209,747 A | 5/1993 | Knoepfler | 606/16 |
| 5,217,460 A | 6/1993 | Knoepfler | 606/52 |
| 5,222,960 A * | 6/1993 | Poley | 606/107 |
| 5,271,379 A | 12/1993 | Phan et al. | 128/4 |

(List continued on next page.)

FOREIGN PATENT DOCUMENTS

| | | | |
|---|---|---|---|
| WO | WO 98/03136 | 1/1998 | |
| WO | WO 99/30644 | 6/1999 | A61F/2/14 |
| WO | WO 99/30645 | 6/1999 | A61F/2/14 |
| WO | WO 99/30656 | 6/1999 | A61F/9/013 |
| WO | WO 99/63912 | 12/1999 | |

OTHER PUBLICATIONS

Grieshaber Knives Brochure, Product Nos. 201–265, Feb. 1997, 3 pages.
"The Grieshaber Microsurgery Knives Ultrasharp" Brochure, Dec. 1996, 4 pages.
"The Grieshaber Microsurgery Knives Ultrathin" Brochure, Jan. 1997, 2 pages.
"The Grieshaber Ruby Knives" Brochure, May 1995, 2 pages.
"The Grieshaber Diamond Knives" Brochure, May 1995, 2 pages.
"The Grieshaber UltraVit Instruments for Vitreoretinal Surgery" Brochure, Jun. 1998, 2 pages.
Grieshaber "Instruments for Irrigation Aspiration" Brochure, Feb. 1997, 1 page.
Alcon 1997–1998 Catalog, "Cutting Instruments, Cannulas & Cystitomes, Ophthalmic Sponges, OPTEMP Cautery", pp. 1–6.
Katena Eye Instruments Catalog Supplement; 1997, pp. 87, 92.

*Primary Examiner*—Cary E. O'Connor
(74) *Attorney, Agent, or Firm*—W. David Lee

(57) ABSTRACT

A microsurgical instrument having a handle and a dissecting tip coupled to the handle is disclosed. The handle includes a cannula for transporting surgical fluid. The dissecting tip includes a blade for dissecting tissue and an aperture for delivering the fluid. The instrument may be used to more effectively create an intracorneal pocket for the implantation of an intracorneal optical lens.

16 Claims, 4 Drawing Sheets

U.S. PATENT DOCUMENTS

| | | | |
|---|---|---|---|
| 5,300,087 A | 4/1994 | Knoepfler | 606/207 |
| 5,336,235 A * | 8/1994 | Myers et al. | 606/166 |
| 5,370,652 A | 12/1994 | Kellan | 606/166 |
| 5,665,100 A | 9/1997 | Yoon | 606/170 |
| 5,683,592 A * | 11/1997 | Bartholomew et al. | 216/24 |
| 5,755,700 A | 5/1998 | Kritzinger et al. | 604/257 |
| 5,808,665 A | 9/1998 | Green | 348/65 |
| 5,893,863 A | 4/1999 | Yoon | 606/170 |
| 5,897,507 A | 4/1999 | Kortenbach et al. | 600/562 |
| 5,919,202 A | 7/1999 | Yoon | 606/170 |
| 5,944,752 A | 8/1999 | Silvestrini | 623/5 |
| 5,964,776 A | 10/1999 | Peyman | 606/166 |
| 6,036,709 A * | 3/2000 | Boutros | 606/166 |

* cited by examiner

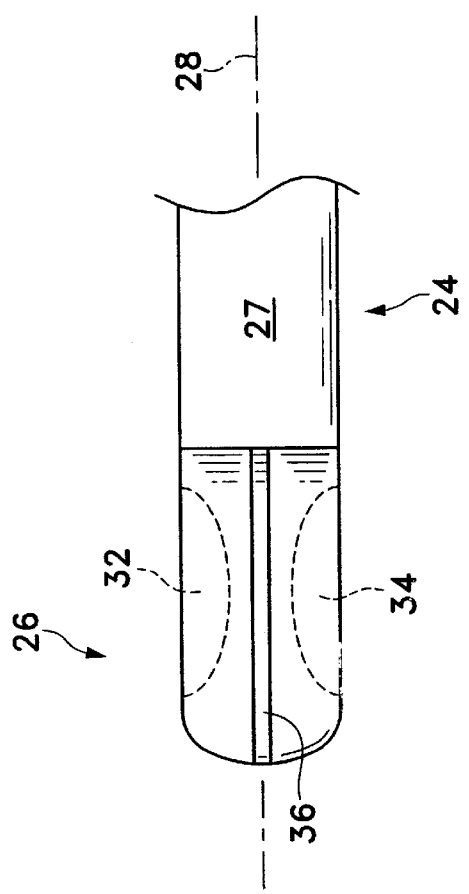
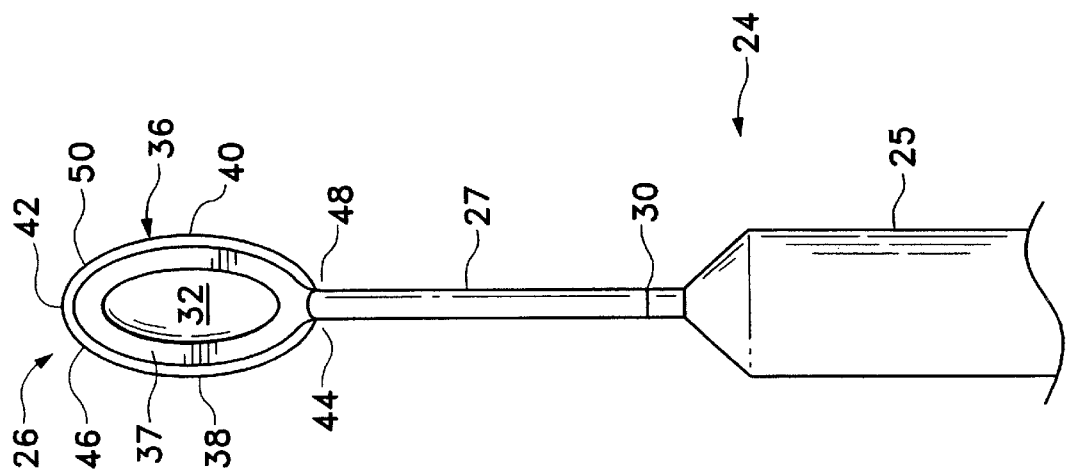
FIG. 2
FIG. 3

LAMELLAR DISSECTING INSTRUMENT

This application is a continuation-in-part of U.S. application Ser. No. 09/434,912 filed Nov. 5, 1999, pending.

FIELD OF THE INVENTION

The present invention relates generally to microsurgical instruments and more specifically, but not by way of limitation, to microsurgical instruments suitable for creating a corneal pocket incision for the implantation of intracorneal optical lenses (ICOLs).

DESCRIPTION OF THE RELATED ART

The human eye in its simplest terms functions to provide vision by transmitting light through a clear outer portion called the cornea, and focusing the image by way of a crystalline lens onto a retina. The quality of the focused image depends on many factors including the size and shape of the eye, and the transparency of the cornea and the lens.

The optical power of the eye is determined by the optical power of the cornea and the crystalline lens. In the normal, healthy eye, sharp images are formed on the retina (emmetropia). In many eyes, images are either formed in front of the retina because the eye is abnormally long (axial myopia), or formed in back of the retina because the eye is abnormally short (axial hyperopia). The cornea also may be asymmetric or toric, resulting in an uncompensated cylindrical refractive error referred to as corneal astigmatism. In addition, due to age-related reduction in lens accommodation, the eye may become presbyopic resulting in the need for a bifocal or multifocal correction device.

In the past, axial myopia, axial hyperopia and corneal astigmatism generally have been corrected by spectacles or contact lenses, but there are several refractive surgical procedures that have been investigated and used since 1949. Barraquer investigated a procedure called keratomileusis that reshaped the cornea using a microkeratome and a cryolathe. This procedure was never widely accepted by surgeons. Another procedure that has been used is radial and/or transverse incisional keratotomy (RK or AK, respectively). Photoablative lasers have also been used to reshape the surface of the cornea (photorefractive keratectomy or PRK) or for mid-stromal photoablation (Laser-Assisted In Situ Keratomileusis or LASIK). All of these refractive surgical procedures cause an irreversible modification to the shape of the cornea in order to effect refractive changes, and if the correct refraction is not achieved by the first procedure, a second procedure or enhancement must be performed. Additionally, the long-term stability of the correction is variable because of the variability of the biological wound healing response between patients.

Permanent intracorneal implants made from synthetic materials are also known for the correction of corneal refractive errors. Such implants may be generally classified into two categories.

One category is intracorneal implants that have little or no refractive power themselves, but change the refractive power of the cornea by modifying the shape of the anterior surface of the cornea. U.S. Pat. No. 5,123,921 (Werblin, et al.); U.S. Pat. Nos. 5,505,722, 5,466,260, 5,405,384, 5,323, 788, 5,318,047, 5,312,424, 5,300,118, 5,188,125, 4,766,895, 4,671,276 and 4,452,235 owned by Keravision and directed to intrastromal ring devices; and U.S. Pat. No. 5,090,955 (Simon), U.S. Pat. No. 5,372,580 (Simon, et al.), and WIPO Publication No. WO 96/06584 directed to Gel Injection Adjustable Keratoplasty (GIAK) all disclose examples of this category of implant.

A second category is intracorneal implants having their own refractive power. U.S. Pat. No. 4,607,617 (Choyce); U.S. Pat. No. 4,624,669 (Grendahl); U.S. Pat. No. 5,628,794 (Lindstrom); and U.S. Pat. Nos. 5,196,026 and 5,336,261 (Barrett, et al.) provide several examples of this category. In addition, U.S. patent application Ser. No. 08/908,230 filed Aug. 7, 1997 entitled "Intracorneal Diffractive Lens", which is incorporated herein in its entirety by reference, discloses an example of an ICOL that has both refractive and diffractive powers.

Microsurgical instruments used for the implantation of such intracorneal implants have also been developed. For example, WIPO Publication No. WO 99/30645 owned by Keravision discloses a variety of instruments for surgically implanting ring-shaped intracorneal implants and ICOLs. These tools may be used manually, but are preferably used in cooperation with a vacuum centering device. The surgical procedures described in this publication require multiple instruments to form an intracorneal ring-shaped channel or an intracorneal pocket. In addition, the use of a vacuum centering device increases the expense of the surgical procedure.

Accordingly, a need exists for a microsurgical instrument that more effectively creates an intracorneal pocket for the implantation of an ICOL. The instrument should be easy for the surgeon to use, should maximize patient safety, and should be economically feasible. The instrument should eliminate the need for multiple tools for forming the intracorneal pocket.

SUMMARY OF THE INVENTION

One aspect of the present invention is a microsurgical instrument having a handle and a dissecting tip coupled to the handle. The handle includes a cannula for transporting surgical fluid. The dissecting tip includes a blade for dissecting tissue and an aperture for delivering the fluid.

Another aspect of the present invention is a method of creating an intracorneal pocket for the implantation of an intracorneal optical lens. A microsurgical instrument is provided. The instrument has a handle and a dissecting tip coupled to the handle. The handle includes a cannula for fluidly coupling to a reservoir of surgical fluid. The dissecting tip includes a blade for dissecting tissue and an aperture for delivering the fluid. The dissecting tip is inserted into an incision into a cornea. The reservoir is activated to eject the surgical fluid from the aperture. The intracorneal pocket is created by moving the tip in an arcuate, planar manner. The surgical fluid facilitates the dissection of stromal tissue. The surgical fluid also lubricates the dissecting tip so as to minimize irritation of stromal tissue.

BRIEF DESCRIPTION OF THE DRAWINGS

For a more complete understanding of the present invention, and for further objects and advantages thereof, reference is made to the following description taken in conjunction with the accompanying drawings in which:

FIG. 2 is an enlarged, side view of a preferred embodiment of the dissecting tip of the microsurgical instrument of FIG. 1;

FIG. 3 is an enlarged, top view of a preferred embodiment of the dissecting tip of the microsurgical instrument of FIG. 1;

DETAILED DESCRIPTION OF THE PREFERRED EMBODIMENTS

The preferred embodiments of the present invention and their advantages are best understood by referring to FIGS. 1 through 6 of the drawings, like numerals being used for like and corresponding parts of the various drawings.

Figure 1:
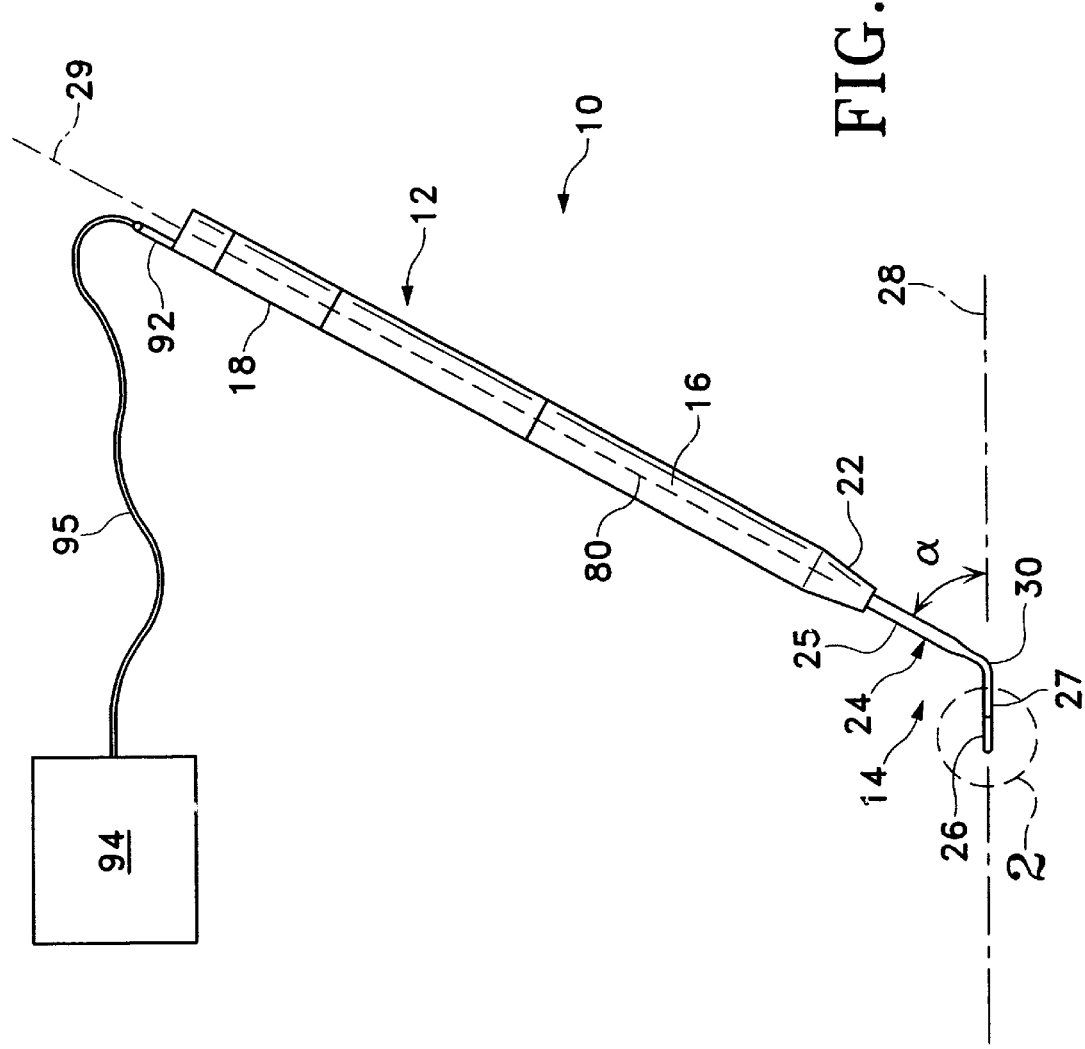
FIG. 1 is a side view schematically illustrating a microsurgical instrument according to a preferred embodiment of the present invention.

FIG. 1 illustrates a microsurgical instrument 10 according to a preferred embodiment of the present invention. Instrument 10 is preferably a lamellar dissecting tool for use in creating a corneal pocket incision for the implantation of intracorneal optical lenses (ICOLs). However, instrument 10 may be used for dissecting lamellar tissue at locations other than the eye. For convenience of description, but not by way of limitation, the present invention will be described hereinbelow with reference to a lamellar dissecting instrument 10 for use in creating a corneal pocket incision.

Instrument 10 includes a handle 12 and a dissecting tip 14. Handle 12 preferably has a generally cylindrical geometry and preferably includes a region 16 having a knurled or roughened surface to facilitate the gripping of instrument 10. Handle 12 may also have a generally flat region 18 that allows instrument 10 to be marked with identifying data. Handle 12 is preferably made out of conventional thermoset polymeric materials. Handle 12 may alternatively be formed from surgical stainless steel or other conventional materials used to form microsurgical instruments, if desired. Dissecting tip 14 is coupled to a distal end 22 of handle 12. As shown in FIG. 1, such coupling is formed by an interference fit and/or epoxy. Alternatively, distal end 22 of handle 10 may include a conventional connecting hub (not shown) such as a collet or other clamping mechanism for removably coupling with dissecting tip 14. Such a connecting hub allows for the substitution of different blades or tips on instrument 10.

Dissecting tip 14 generally includes a neck 24 and a blade 26. Neck 24 has a proximal portion 25 and a distal portion 27. Distal portion 27 and blade 26 preferably have a common longitudinal axis 28. Proximal portion 25 and handle 12 preferably have a common longitudinal axis 29. Distal portion 27 preferably has a bend 30 to facilitate manipulation of blade 26 by a surgeon. Bend 30 positions distal portion 27 and blade 26 at an angle α with respect to proximal portion 25 and handle 12. Angle α is preferably from about 30 degrees to about 60 degrees, and is most preferably about 45 degrees. Blade 26 preferably has a length of about 4 mm to about 5.5 mm, a maximum width of about 2 mm to about 3 mm, and a maximum thickness of about 0.48 mm to about 0.6 mm. Most preferably, blade 26 has a length of about 4 mm, a maximum width of about 2 mm, and a maximum thickness of about 0.48 mm. Distal portion 27 of neck 24 preferably has a length of about 6.5 mm to about 8 mm, a width of about 0.75 mm to about 1 mm, and a thickness of about 0.48 mm to about 0.6 mm. Most preferably, distal portion 27 of neck 24 has a length of about 8 mm, a width of about 0.75 mm, and a thickness of about 0.48 mm. Proximal portion 25 of neck 24 preferably has a length of about 10.3 mm, a width of about 2.8 mm, and thickness of about 0.6 mm. The length of dissecting tip 14 from the distal end of blade 26 to bend 30 is preferably about 10 mm to about 10.5 mm. Most preferably, this length is about 10 mm. Neck 24 and blade 26 are preferably integrally formed from surgical stainless steel or other conventional material used for microsurgical instrument blades.

Neck 24 and blade 26 are more clearly shown in the enlarged, side view of FIG. 2 and the enlarged, top view of FIG. 3. Blade 26 preferably has a generally elliptical, three dimensional geometry with a depression 32 on its top surface and a depression 34 on its bottom surface. As shown in FIG. 3, depression 32 preferably has a generally elliptical shape from a top view. Similarly, depression 34 preferably has a generally elliptical shape from a bottom view. Alternatively, blade 26 may be formed without depressions 32 and 34, if desired. Blade 26 has an edge 36 formed around its periphery. Edge 36 is preferably formed so that it is sharp enough to easily delaminate layers of corneal stroma during creation of an intracorneal pocket, but not sharp enough to easily cut the stromal tissue. Edge 36 is preferably formed with an edge radius between about 0.001 inches to about 0.025 inches, and more preferably about 0.005 inches. Depression 32 and edge 36 define a generally elliptical, convex, ring shaped surface 37 for contacting and delaminating the stromal tissue. Similarly, depression 34 and edge 36 define a generally elliptical, convex, ring shaped surface 39 (not shown) for contacting and delaminating the stromal tissue. It has been found that when blade 26 having depressions 32 and 34 is used to create an intracorneal pocket, it exhibits less drag or friction on stromal tissues than a similarly shaped blade having no depressions 32 and 34. Reducing such drag correspondingly reduces the trauma to the stromal tissues, as well as the chance of accidentally tearing the stromal tissues.

Edge 36 preferably comprises three arcs 38, 40, and 42. Arc 38 includes the portion of edge 36 between a point 44 proximate distal portion 27 of neck 24 to a point 46 proximate a distal end of blade 26. Arc 38 preferably has a length of about 3.7 mm to about 5.2 mm. For example, in an intracorneal pocket having a diameter of about 8 mm that is created using a tunnel incision having a width of about 3 mm, blade 26 may have a length of about 4 mm, a width of about 2 mm, and an arc 38 having a length of about 3.7 mm. This length of arc 38 may be defined by moving a radius of curvature of about 4 mm through an angle of rotation of about 53.4 degrees. As another example, in an intracorneal pocket having a diameter of about 8 mm that is created using a tunnel incision having a width of about 3 mm, blade 26 may have a length of about 5.5 mm, a width of about 3 mm, and an arc 38 having a length of about 5.2 mm. This length of arc 38 may be defined by moving a radius of curvature of about 4 mm through an angle of rotation of about 74.2 degrees. Arc 40 generally opposes arc 38 and includes the portion of edge 36 between a point 48 proximate distal portion 27 of neck 24 and a point 50 proximate the distal end of blade 26. Arc 40 preferably has an identical length, and is preferably formed in an identical manner, as arc 38. Arc 42 includes the portion of edge 36 between points 46 and 50. Arc 42 prevents blade 26 from having a sharp distal tip that would be prone to cut, instead of delaminate, stromal tissue. The length of arc 42 is dependent on the separation between arcs 38 and 40. For example, if blade 26 has a width of about 2 mm, arc 42 preferably has a length of about 1.9 mm. This length may be defined by moving a radius of curvature of about 0.8 mm through an angle of rotation of about 138 degrees. As another example, if blade 26 has a width of about 3 mm, arc 42 preferably has a length of about 2.0 mm. This length may be defined by moving a radius of curvature of about 1.0 mm through an angle of rotation of about 114 degrees.

Figure 4:
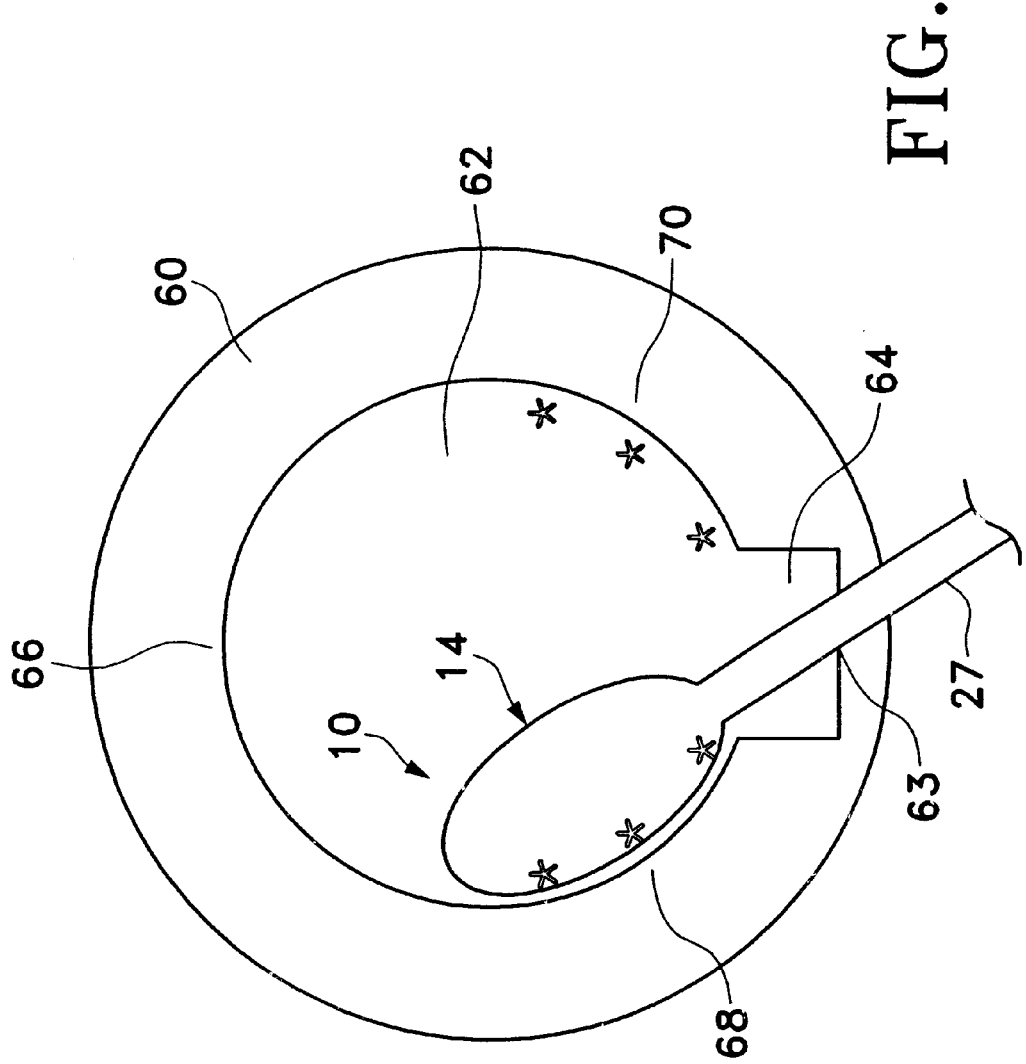
FIG. 4 is an enlarged, top view schematically illustrating the creation of an intracorneal pocket using the microsurgical instrument of FIG. 1.

Referring now to FIGS. 1–4, the preferred method of using lamellar dissecting instrument 10 to create an intracorneal pocket for the insertion of an ICOL will now be described in greater detail. As shown in FIG. 4, a human eye has a cornea 60 having a diameter of about 12 mm. Therefore, the diameter of an ICOL (not shown) must be less than 12 mm, is preferably from about 5 mm to about 9 mm, and is most preferably about 7 mm. Intracorneal pocket 62 for receiving the ICOL preferably has a diameter about 1 mm larger than the diameter of the ICOL. For the preferred ICOL having a diameter of about 7 mm, intracorneal pocket 62 has a diameter of about 8 mm. For convenience of description, but not by way of limitation, the preferred method of creating an intracorneal pocket with lamellar dissecting instrument 10 will be described with reference to an intracorneal pocket 62 having a diameter of about 8 mm.

During the procedure, a surgeon uses an operating microscope to visualize the anterior aspect of eye. The surgeon first applies a topical anesthetic to the eye. A fine Thorton ring, a Kremer forceps, or similar conventional instrument is used to secure the eye from rotating. A conventional 8 mm optical zone marker is placed on the cornea centered on the visual axis of the eye. A conventional 3 mm optical zone marker is placed on the cornea adjacent the 8 mm optical zone marker, preferably at the twelve o'clock position. The surgeon determines the thickness of cornea 60 at a center 63 of the 3 mm optical zone mark using conventional ultrasound pachymetry. The surgeon then sets a conventional surgical diamond knife to about sixty percent of the pachymetry reading, and makes an incision parallel to the limbus at center 63. The surgeon creates a tunnel incision 64 into cornea 60 at center 63 using a Paufique Duredge knife, Suarez spreader, or similar conventional instrument. Tunnel incision 64 preferably has a width of about 3 mm, a length of about 1.5 mm, and a depth of about 0.25 mm to about 0.3 mm from the outer surface of cornea 60. The depth of tunnel incision 64 is preferably selected to dispose edge 36 of blade 26 at about the midplane of the desired intracorneal pocket 62. The surgeon removes the knife used to create tunnel incision 64, and inserts tip 14 of instrument 10 into tunnel incision 64, with edge 36 of blade 26 being disposed on the midplane of the desired pocket 62. Tip 14 preferably does not enlarge tunnel incision 64.

The surgeon then creates intracorneal pocket 62 using a series of arcuate, planar movements of tip 14. Because of the width of distal portion 27 of neck 24, the arcuate movements of tip 14 do not result in neck 24 contacting the sides of tunnel incision 64, avoiding trauma to stromal tissue. Due to the length of blade 26 and distal portion 27 of neck 24, tip 14 may easily reach the desired distal end 66 of pocket 62. In addition, due to the curvature of arcs 38 and 40, tip 14 can be used to create a circular pocket 62 even at "blind spots" 68 and 70, which are indicated by asterisks in FIG. 4. Edge 36 and surfaces 37 and 39 function primarily to dissect or delaminate stromal tissue. Depressions 32 and 34 function primarily to reduce the drag on, and associated trauma to, stromal tissue.

After formation of pocket 62, the surgeon removes tip 14 of instrument 10, and then implants an ICOL into pocket 62 using forceps or a similar conventional instrument. A forceps particularly useful for implanting an ICOL is disclosed in U.S. Pat. No. 6,290,705, which is incorporated herein in its entirety by this reference. A topical antibiotic/steroid solution is placed in the eye after implantation. If the explanting of the ICOL is necessary at a later time, arc 42 of blade 26 is preferably sharp enough to re-open tunnel incision 64 after the incision has healed.

Figure 6:
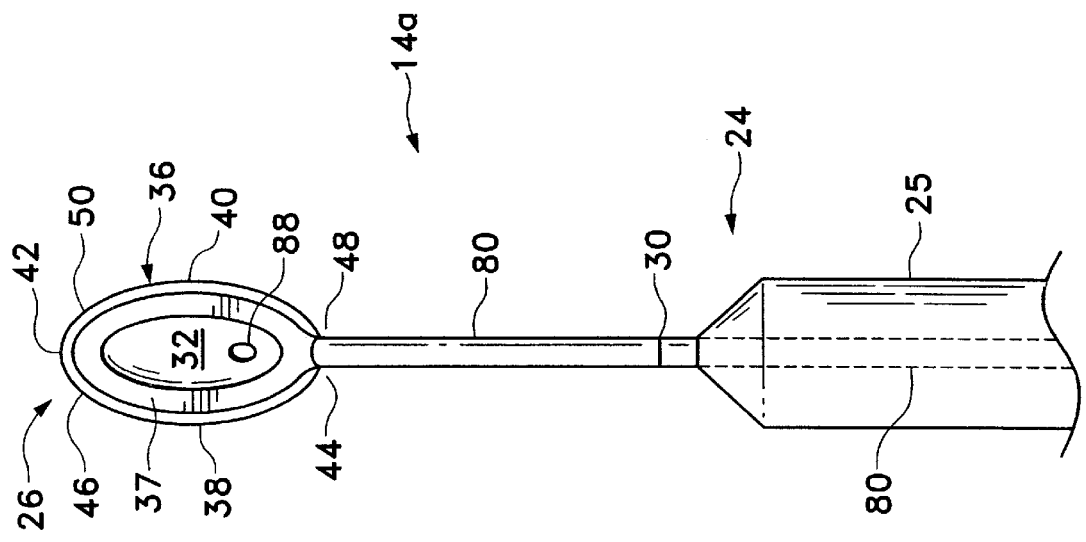
FIG. 6 is an enlarged, top view of a second preferred embodiment of the dissecting tip of the microsurgical instrument of FIG. 1.
Figure 5:
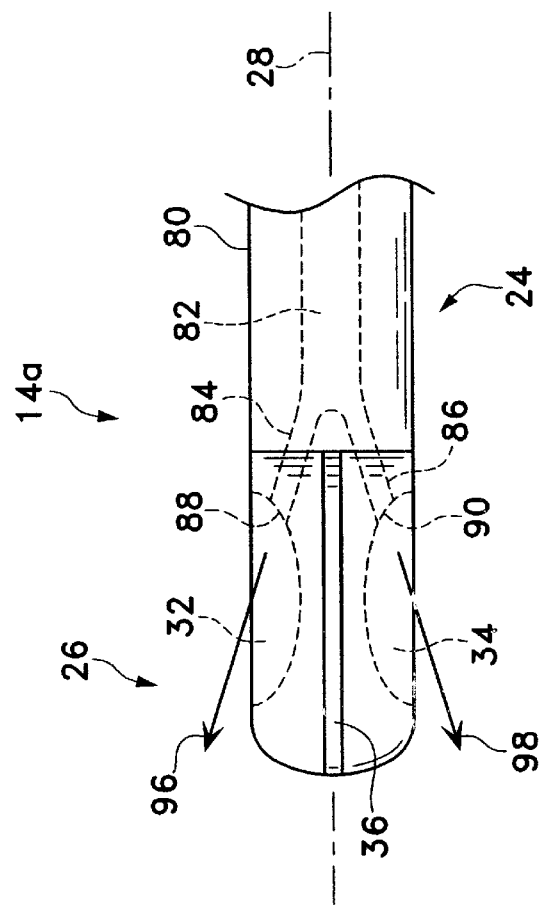
FIG. 5 is an enlarged side view of a second preferred embodiment of the dissecting tip of the microsurgical instrument of FIG. 1.

Referring now to FIGS. 5 and 6, an enlarged view of a second preferred embodiment of the dissecting tip of microsurgical instrument 10 is schematically illustrated. In this embodiment, instrument 10 has a dissecting tip 14a. The structure and operation of dissecting tip 14a is identical to that described above for dissecting tip 14 with several exceptions. First, distal portion 27 of neck 24 is replaced with a cannula 80. Cannula 80 is formed with the same external geometry and dimensions as distal portion 27. Cannula 80 preferably has a width of about 0.75 mm and a thickness of about 0.48 mm. In addition, cannula 80 has an internal bore 82 for the passage of a surgical fluid. At its distal end, bore 82 preferably splits into internal bores 84 and 86. Bore 84 preferably terminates in an aperture 88 disposed on depression 32. Bore 86 preferably terminates in an aperture 90 disposed on depression 34. Although not shown in FIGS. 5 and 6, apertures 88 and 90 may be located on portions of blade 26 other than depressions 32 and 34, if desired. As shown in FIG. 6, cannula 80 may be disposed within, or coupled to an exterior surface of, proximal portion 25 of neck 24. Cannula 80 is preferably formed from surgical stainless steel.

Referring to FIG. 1, cannula 80 is also disposed within, or coupled to an exterior surface of, handle 12. The proximal end of cannula 80 preferably extends from the proximal end of handle 12 and terminates in a port 92. Port 92 is for fluidly coupling with a reservoir 94. Such coupling is preferably performed using medical grade silastic tubing 95. Reservoir 94 may comprise a syringe, a pumping device, or other conventional apparatus for providing pressurized surgical fluid.

Referring to FIGS. 1 and 4–6, when a surgeon moves tip 14a of lamellar dissecting instrument 10 in a series of arcuate, planar movements to create intracorneal pocket 62, the surgeon may also activate reservoir 94 to provide surgical fluid to apertures 88 and 90 via cannula 80. Surgical fluid is ejected from apertures 88 and 90. Surgical fluid is preferably ejected with enough force to facilitate the dissection or delamination of stromal tissue. Apertures 88 and 90 are preferably formed so that a stream of fluid is ejected from each aperture, as indicated by arrows 96 and 98 in FIG. 5. Apertures 88 and 90 are preferably oriented so that the streams of surgical fluid are ejected out and away from longitudinal axis 28 of blade 26. The surgical fluid lubricates tip 14a during the formation of intracorneal pocket 62 and during the withdrawal of tip 14a from tunnel incision 64, minimizing any irritation of the stromal tissues. After withdrawal of tip 14a, any excess surgical fluid drains out of intracorneal pocket 62 into the exterior of the cornea.

From the above, it may be appreciated that the present invention provides a microsurgical instrument that more effectively creates an intracorneal pocket for the implantation and explantation of an ICOL. The instrument is easy for the surgeon to use and is relatively inexpensive. The instrument eliminates the need for multiple tools for forming the intracorneal pocket, simplifying the surgical procedure and maximizing patient safety.

The present invention is illustrated herein by example, and various modifications may be made by a person of ordinary skill in the art. For example, the length of blade 26 and neck 24 may be changed to accommodate the formation of intracorneal pockets having various diameters. As another example, the geometries of handle 12 and neck 24 may be different from that shown in the preferred embodiment. As a further example, the three dimensional geometry of blade 26 may be a shape other than an ellipse, as long as blade 26 has a generally elliptical shape from a top view. As a further example, dissecting tip 14*a* may be formed with only one aperture for the delivery of a surgical fluid, or more than two apertures for the delivery of a surgical fluid. As a further example, cannula 80 may be used to deliver a pharmaceutical preparation. As a final example, although the preferred instrument is described hereinabove as a lamellar dissecting instrument for the implantation of an ICOL, the present invention is applicable to instruments used for dissecting lamellar tissue at locations other than the eye.

It is believed that the operation and construction of the present invention will be apparent from the foregoing description. While the apparatus and methods shown or described above have been characterized as being preferred, various changes and modifications may be made therein without departing from the spirit and scope of the invention as defined in the following claims.

What is claimed is:

1. An ophthalmic microsurgical instrument for creating an intracorneal pocket, comprising:
   a handle having a cannula for transporting surgical fluid; and
   a dissecting tip coupled to said handle, said tip comprising a blade having a generally elliptical, non-spherical three-dimensional geometry and an aperture for delivering said fluid, wherein said blade comprises a first depression on a top surface and a second depression on a bottom surface.

2. The microsurgical instrument of claim 1 wherein said cannula is for fluidly coupling to a reservoir of surgical fluid, and said aperture is for ejecting a stream of said fluid.

3. The microsurgical instrument of claim 1 wherein said aperture is disposed in one of said first depression or said second depression.

4. The microsurgical instrument of claim 1 wherein said blade comprises a second aperture for delivering said fluid.

5. The microsurgical instrument of claim 1 wherein:
   said blade comprises a second aperture for delivering said fluid;
   said first aperture is disposed in said first depression; and
   said second aperture is disposed in said second depression.

6. A method of creating an intracorneal pocket for the implantation of an intracorneal optical lens, comprising the steps of:
   providing an instrument, comprising:
      a handle having a cannula for fluidly coupling to a reservoir of surgical fluid; and
      a dissecting tip coupled to said handle, said tip comprising a blade having a generally elliptical, non-spherical three-dimensional geometry and an aperture for delivering said fluid;
   inserting said tip into an incision into a cornea;
   activating said reservoir to eject said fluid from said aperture; and
   creating said pocket by moving said tip in an arcuate, planar manner.

7. The method of claim 6 wherein said activating step facilitates the dissection of stromal tissue.

8. The method of claim 6 wherein said activating step lubricates said dissecting tip so as to minimize irritation of stromal tissue.

9. An ophthalmic microsurgical instrument for creating an intracorneal pocket, comprising:
   a handle having a cannula for transporting surgical fluid; and
   a dissecting tip coupled to said handle, said tip comprising a blade having an edge with a generally elliptical, non-circular shape, said blade having an aperture for delivering said fluid, wherein said blade comprises a first depression on a top surface and a second depression on a bottom surface.

10. The microsurgical instrument of claim 9 wherein said cannula is for fluidly coupling to a reservoir of surgical fluid, and said aperture is for ejecting a stream of said fluid.

11. The microsurgical instrument of claim 9 wherein said aperture is disposed in one of said first depression or said second depression.

12. The microsurgical instrument of claim 9 wherein said blade comprises a second aperture for delivering said fluid.

13. The microsurgical instrument of claim 9 wherein:
   said blade comprises a second aperture for delivering said fluid;
   said first aperture is disposed in said first depression; and
   said second aperture is disposed in said second depression.

14. A method of creating an intracorneal pocket for the implantation of an intracorneal optical lens, comprising the steps of:
   providing an instrument, comprising:
      a handle having a cannula for fluidly coupling to a reservoir of surgical fluid; and
      a dissecting tip coupled to said handle, said tip comprising a blade having an edge with a generally elliptical, non-circular shape, said blade having an aperture for delivering said fluid;
   inserting said tip into an incision into a cornea;
   activating said reservoir to eject said fluid from said aperture; and
   creating said pocket by moving said tip in an arcuate, planar manner.

15. The method of claim 14 wherein said activating step facilitates the dissection of stromal tissue.

16. The method of claim 14 wherein said activating step lubricates said dissecting tip so as to minimize irritation of stromal tissue.

* * * * *